US010549897B2

(12) United States Patent
Sacks

(10) Patent No.: US 10,549,897 B2
(45) Date of Patent: Feb. 4, 2020

(54) ENCLOSURE AND METHOD FOR PREVENTION OF HEALTH-CARE-ASSOCIATED INFECTIONS FROM CONTAMINATED DEVICES

(71) Applicant: Kenneth R. Sacks, Santa Monica, CA (US)

(72) Inventor: Kenneth R. Sacks, Santa Monica, CA (US)

( * ) Notice: Subject to any disclaimer, the term of this patent is extended or adjusted under 35 U.S.C. 154(b) by 761 days.

(21) Appl. No.: 14/035,736

(22) Filed: Sep. 24, 2013

(65) Prior Publication Data

US 2014/0260091 A1 Sep. 18, 2014

Related U.S. Application Data

(60) Provisional application No. 61/801,758, filed on Mar. 15, 2013.

(51) Int. Cl.
*A61B 46/10* (2016.01)
*B65D 81/18* (2006.01)
(Continued)

(52) U.S. Cl.
CPC ............ *B65D 81/18* (2013.01); *A45C 13/002* (2013.01); *A45C 2011/002* (2013.01);
(Continued)

(58) Field of Classification Search
CPC . A61L 2/26; A61L 2202/181; B32B 2571/00; A61B 1/00142; A61B 46/10
(Continued)

(56) References Cited

U.S. PATENT DOCUMENTS 4,918,839 A * 4/1990 Brandon ................ A43B 3/163 36/7.1 R
5,028,468 A * 7/1991 Taylor ................ A47G 27/0206 428/192
(Continued)

FOREIGN PATENT DOCUMENTS

WO WO 9937233 A1 * 7/1999 ................ A61J 1/00

OTHER PUBLICATIONS

William A. Rutala and David J. Weber, "Guideline for Disinfection and Sterilization in Healthcare Facilities", 2008 (158 pages).

*Primary Examiner* — Andrew M Tecco
*Assistant Examiner* — Eyamindae C Jallow
(74) *Attorney, Agent, or Firm* — Imperium Patent Works; T. Lester Wallace; Amir V. Adibi

(57) ABSTRACT

A novel enclosure is used to prevent health-care-associated infections caused by contamination of devices such as cellular telephones, laptops, tablet computers, purses, and briefcases. Such a device is placed into the enclosure and is carried into a disinfected or clean environment, such as an operating room. The enclosure prevents infectious agents or other contaminants on the surface of the device from contaminating the clean environment. The enclosure also protects the environments outside the operating room from contaminants within the operating room. The enclosure is inexpensively manufactured and disposable. The enclosure may include an effective amount of antibacterial, antifungal, and/or antiviral compounds. The enclosure may be used in the residence of an individual with a compromised immune system. The enclosure may be used to bring a device into and out of a home or room of an individual who is extremely neat or is inflicted with an obsessive-compulsive disorder.

20 Claims, 11 Drawing Sheets

(51) Int. Cl.
*A45C 13/00* (2006.01)
*A61G 10/00* (2006.01)
*A61G 13/10* (2006.01)
*A45C 11/00* (2006.01)

(52) U.S. Cl.
CPC ............ *A61G 10/005* (2013.01); *A61G 13/10* (2013.01); *A61G 2210/30* (2013.01)

(58) Field of Classification Search
USPC ..................... 53/397; 604/171; 128/849, 853
See application file for complete search history.

(56) References Cited

U.S. PATENT DOCUMENTS

| | | | | |
|---|---|---|---|---|
| 5,142,736 | A * | 9/1992 | Kuehn | A61G 15/10 16/421 |
| 5,302,124 | A * | 4/1994 | Lansing | A61C 19/004 150/154 |
| 5,782,821 | A * | 7/1998 | Couch | A61B 46/10 383/71 |
| 5,812,188 | A * | 9/1998 | Adair | A61B 1/00039 128/849 |
| 5,926,888 | A | 7/1999 | Chen et al. | 12/142 |
| 5,957,381 | A * | 9/1999 | Wakamatsu | F02M 45/08 239/88 |
| 6,023,856 | A | 2/2000 | Brunson et al. | 36/7.1 |
| 6,067,731 | A | 5/2000 | Chen et al. | 36/7.3 |
| 6,330,721 | B1 | 12/2001 | Wallace et al. | 2/174 |
| 6,532,686 | B2 | 3/2003 | Gultekin et al. | 36/7.1 R |
| 6,911,022 | B2 * | 6/2005 | Steger | A61F 13/84 604/385.04 |
| 6,931,767 | B2 | 8/2005 | Royle | 36/111 |
| 9,168,102 | B2 * | 10/2015 | Ryterski | A61B 19/081 |
| 2003/0097043 | A1 * | 5/2003 | Ouchi | A61B 1/00142 600/122 |
| 2006/0020166 | A1 * | 1/2006 | Berall | A61B 1/00142 600/121 |
| 2006/0131190 | A1 * | 6/2006 | Weaver | G06F 3/039 206/305 |
| 2007/0213835 | A1 | 9/2007 | Wimmer et al. | 623/23.58 |
| 2008/0055820 | A1 * | 3/2008 | Coleman | H04B 1/3888 361/600 |
| 2010/0048267 | A1 | 2/2010 | Lin | 455/575.8 |
| 2011/0019939 | A1 * | 1/2011 | Schwarz | B65D 33/04 383/12 |
| 2011/0192744 | A1 * | 8/2011 | Parker | A61B 1/00059 206/363 |
| 2014/0251345 | A1 * | 9/2014 | Fleming | A61B 19/081 128/849 |

* cited by examiner

DRAW STATION DISPENSER
FOR CELL PHONE SLIP ON COVERS

LENGTHWISE CROSS-SECTIONAL SIDE VIEW OF A
CELL PHONE IN A SLIP ON COVER

WIDTHWISE CROSS-SECTIONAL SIDE VIEW OF A CELL PHONE IN THE SLIP ON COVER OF FIG. 13

LENGTHWISE CROSS-SECTIONAL SIDE VIEW OF A CELL PHONE IN THE SLIP ON COVER OF FIG. 13

WIDTHWISE CROSS-SECTIONAL SIDE VIEW OF A CELL PHONE IN THE SLIP ON COVER OF FIG. 13

ENCLOSURE AND METHOD FOR PREVENTION OF HEALTH-CARE-ASSOCIATED INFECTIONS FROM CONTAMINATED DEVICES

CROSS REFERENCE TO RELATED APPLICATION

This application claims the benefit under 35 U.S.C. § 119 from provisional U.S. patent application Ser. No. 61/801,758, entitled "Enclosure and Method for Prevention of Health-Care-Associated Infections from Contaminated Devices," filed on Mar. 15, 2013, the subject matter of which is incorporated herein by reference.

BACKGROUND INFORMATION

The surfaces of medical equipment and other device surfaces may become contaminated with infectious agents and may cause health-care-associated infections. For example, hospital floors may become contaminated with microorganisms from settling airborne bacteria, from spills, or by contact with shoes, wheels or other devices such as cellular phones, laptops, purses, and satchels. Surfaces of hospital beds, blood pressure cuffs, stethoscopes, and X-Ray machines may be contaminated by hand or by other bodily contact. Disinfection of these surfaces is essential to ensure that infectious pathogens are not transmitted to health care patients. Disinfectants may be used to effectively eliminate or reduce the possibility of these health-care-associated infections caused by contamination of medical equipment. Therefore, the surfaces of medical equipment and objects must be wiped with disinfectants to prevent health-care-associated infections in patients and other health care professionals. But these surfaces can become re-contaminated subsequent to disinfection through contact with other contaminated objects.

Cellular phones are often used in hospitals by healthcare professionals, patients and visitors. The surfaces of cellular phones are in frequent contact with the face, mouth, ears and hands of the cellular telephone user and likely carry a variety of bacteria and other infectious agents. Unlike hands which are easily sterilized using disinfectants, cellular phones are rarely cleaned and therefore may easily cause contamination or recontamination of the surfaces of medical and other equipment.

FIG. 1 (Prior Art) is a drawing of a cellular telephone 1. Cellular telephone 1 includes a touchpad 2. The touchpad 2 of cellular telephone 1 is frequently "touched" with the hands or fingers of the cellular telephone user. The touchpad 2 is also in frequent contact with the face and ears of the user of cellular telephone 1 and may become contaminated with infectious agents.

FIG. 2 (Prior Art) is another drawing of the cellular telephone 1 of FIG. 1 and includes touchpad 2 and bottom surface 3. Bottom surface 3 of cellular telephone 1 is also frequently held with the hands of the user of the telephone and may also become contaminated with infectious agents. When cellular telephone 1 comes in contact with the surfaces of medical equipment, the medical equipment may become contaminated with the infectious agents from the surfaces of the cellular telephone. Also, touchpad 2, bottom surface 3, and other surfaces of cellular telephone 1 may not be smooth and may have gaps or indentations and therefore may be difficult to remove the infectious agents by wiping of the cellular telephone 1 with a disinfectant. Moreover, using a liquid disinfectant on the surfaces of cellular telephone 1 may damage the telephone. The surfaces of cellular phones are not the only likely sources of contamination, surfaces of laptop computers, tablet computers, purses, satchels, briefcases and other devices may also be contaminated with infectious agents and may cause subsequent contamination of the surfaces of medical equipment. Healthcare professionals are aware that cellular telephones and other devices that are contaminated with infectious agents are likely to cause health-care-associated infections.

FIG. 3 (Prior Art) is a drawing showing a plastic bag 5. Plastic bag 5 has a smooth nonporous surface and includes the cellular telephone 1 of FIG. 1 and a briefcase 6. By placing devices such as cellular telephones, laptop computers, tablet computers, purses and briefcases into plastic bag 5, the devices will not be in contact with the surfaces of medical equipment. Moreover, if the surface of plastic bag 5 is disinfected, contamination caused by contact between the plastic bag 5 and the surfaces of medical equipment is less likely. There are shortcomings to this method of using a plastic bag to prevent health-care-associated infections. The bag may be difficult to handle. For example, it may be necessary to use a cellular telephone in a medical environment such as an operating room. A health care professional would have to use both hands to open the plastic bag and would have to hold the bag in one hand while locating the cellular telephone with the other. Contamination may still occur when using a plastic bag to carry devices into a disinfected area. Even though the surface of plastic bag 5 may be disinfected, the surfaces of the cellular phone or other device within plastic bag 5 may be contaminated with infectious agents. When the medical professional reaches into the bag to use one of the devices, his hands may come into contact with the contaminated surfaces of the devices inside. Anything that is subsequently touched by the medical professional may become contaminated. A better apparatus and method for prevention of contamination of surfaces, prevention of healthcare-associated-infections, and facilitation of sanitation, is desired.

The dangers of health-care-associated infections are well known in the healthcare industry and guidelines have been published to reduce the occurrence of these infections. One such guideline, "Recommended Practices for Prevention of Transmissible Infections in Perioperative Practice Setting," was published in the AORN Standards, Recommended Practices, and Guidelines, 2007 Edition. One recommended practice from this source is that hand hygiene should be performed any time there is a possibility that there has been contact with blood or other potentially infections materials, and any time when hands may have been soiled or any time the practitioner believes his or her hands may have been soiled.

Another guideline is that protective barriers must be made available to reduce the risk of exposure to potentially infectious material and that personal protective equipment is considered appropriate only if it prevents blood or other potentially infectious material from an employee's contaminated work clothes, undergarments, skin, eyes, mouth, or other mucous membranes under normal conditions of use and for the duration of time for which the protective equipment will be used. Moreover, the guidelines further state that additional protective attire (e.g., liquid-resistant aprons, gowns, shoe covers) should be worn to reduce the risk of exposure to blood, body fluids, or other liquids that may contain potentially infectious agents. There is evidence that supports the need for circulating personnel to wear protective equipment appropriate to the tasks being performed. Fluid-resistant shoe covers are considered part of Personal Protective Equipment (PPE) and must be worn when it can be reasonably anticipated that splashes or spills may occur. Foot attire has no proven significance in reducing the incidence of surgical site wound infections; the primary reason for its use is to facilitate sanitation. If shoe covers are worn, they should be changed whenever they become torn, wet, or soiled, and they should be removed and discarded in a designated container before leaving the surgical area.

The AORN Standards also include guidelines for both low-level and high-level disinfection of items that will enter a surgical suite. This is because patients should be provided a safe, clean environment. A clean surgical environment will reduce the number of microbial flora present. Cleaning and decontamination are the initial and most critical steps in breaking the chain of disease transmission. Cleaning and decontamination of items, equipment, and surfaces before and between procedures will reduce or eliminate microbes such as Hepatitis B Virus (HBV) and Vancomycin-Resistant *Enterococcus* (VRE) which are known to remain viable on the surfaces of operating room equipment and other items for seven days or longer. The cleaning involves all items taken into the operating room setting. Equipment from areas outside the operating room should be damp dusted before being brought into the operating room. Dust and lint are deposited on horizontal surfaces. Proper cleaning of these surfaces helps reduce airborne contaminants that may travel on that dust and lint. Some of the cleaning guidelines include low-level disinfection of items that only come into contact with the intact skin. These are deemed noncritical items and could include handbags, smart phones, laptop or tablet computers, linens, blood pressure cuffs, etc. These items and other equipment contaminated with blood, body fluids, secretions, or excretions should be cleaned and disinfected after each use, according to the healthcare organization's written policy. The use of dedicated patient equipment may be indicated in some situations (e.g., anesthesia, post-anesthesia care units). Routine cleaning of environmental surfaces and items (e.g., laptops, tablet computers, handbags, briefcases, cell and smart-phones) is adequate for inactivation of Methicillin-Resistant *Staphylococcus Aureus* (MRSA), Vancomysin Intermediate Resistant *Staphylococcus aureus* (VISA) and VRE.

Indirect transmission via inanimate surfaces should be prohibited in the operating room and strict adherence to standard precautions minimizes the risk of cross contamination among health care workers, patients, and their environment.

SUMMARY

An enclosure is disclosed for prevention of health-care-associated infections caused by contamination of devices (for example, cellular telephones, laptop and tablet computers, purses, briefcases, and satchels) that are to be brought into disinfected or clean environments, such as operating rooms. The enclosure prevents the spread of infectious agents present on the surfaces of these various devices. When such a device is placed within the enclosure and is carried into the clean environment, the enclosure prevents infectious agents or other contaminants on the surface of the device from contaminating the clean environment. The enclosure is also useful for protecting the environments outside of operating rooms from contaminants in the operating room. If the enclosure becomes contaminated in the operating room, then the enclosure can be removed before contamination from the operating room spreads to areas outside of the operating room. The preferred embodiment of the enclosure is inexpensively manufactured and is disposable. This novel enclosure includes a bag portion with a rim, an opening, and an opening restricting mechanism. The opening restricting mechanism could be an elastic band, drawstring or other type of mechanism that both enlarges and reduces the size of the opening of the enclosure. In one embodiment the enclosure is made of a flexible plastic sheet material that is greater than eight square inches and is less than forty square inches in size. In this embodiment the flexible plastic sheet material is made of a nonporous material that may be disinfected with a medical grade disinfectant. The flexible plastic sheet material may be made of several different types of plastics or a mixture of different plastic materials. The flexible plastic sheet material may be a multi-layer sheet, or a laminated film, of a single-layer sheet. The flexible plastic sheet material may be porous or non-porous.

In one novel use, a cellular telephone is placed within the enclosure by enlarging the opening of the bag portion of the enclosure using the opening restricting mechanism, inserting the cellular phone through the opening, and then reducing the size of the opening with the opening restricting mechanism. In another novel embodiment, the bag portion of the enclosure is transparent and the user of the enclosure can see and access the control buttons of the cellular telephone while it is disposed within the enclosure. In another novel embodiment, a portion of the cellular phone, such as the touchpad is not enclosed by the bag portion and may be directly accessed by the user of the enclosure.

In other embodiments, the enclosure may have an additional opening or openings to accommodate wires used for power connections, earphone and mouthpiece connections, or other similar types of connecting wires. In other novel embodiments still, the enclosure may include fitted bottoms and/or sides to more adequately conform to the shape of devices such as smartphones, tablet or laptop computers, or other electronic devices. The enclosure may be constructed and dimensioned to enclose a particular type of smartphone, tablet or laptop computer, or other electronic device in a snug or tight fitting manner. In one particular embodiment, the enclosure contains an additional pocket structure. This pocket structure may include an alcohol or other type of disinfecting wipe. The alcohol or other disinfecting wipe can also be attached to the enclosure by an adhesive patch, hook and loop fasteners, or in any other similar manner.

In other novel embodiments, the flexible plastic sheet material of the enclosure includes an effective amount of an antibacterial, antifungal, or antiviral material. The antibacterial material may be one of several different types of antibacterial compounds or a mixture thereof. Similarly, an embodiment including an antifungal material or antiviral material may contain one of several different antifungal compounds or antiviral compounds, respectively. In one embodiment, the effective amount of these antibacterial, antifungal, and antiviral compounds is 0.0001 percent to five percent by weight of the flexible plastic sheet material of the enclosure. In another embodiment, an effective amount of a silver-ion based compound is included. These antimicrobial materials may be incorporated into the flexible plastic sheet material by combining the antimicrobial materials with the precursor plastic material prior to bringing the combination of plastic materials and antimicrobial materials to a molten stage or by other methods that are well known in the art. The antimicrobial materials may be provided as part of the flexible plastic sheet material by making a constituent layer of the material contain and hold the antimicrobial material in voids in the plastic material. The antimicrobial materials may be provided as part of the flexible plastic sheet material by coating a constituent layer of the material with the antimicrobial material.

Another embodiment of the novel enclosure contains indicia such as a trade name, advertising, operating instructions, or other indicia. The indicia may be placed on the enclosure by ink-jet printing, silk-screening or any other suitable type of printing process.

The enclosures can also be utilized with larger devices such as briefcases, purses and satchels and these embodiments include a flexible plastic sheet portion in an amount greater than 360 square inches and less than an amount of 1080 square inches. With an enclosure of this size, a healthcare professional or other user can access the contents of a larger device such as a briefcase with minimal or no contact with the contaminated outer surfaces of the briefcase. In still other embodiments, the amount of flexible plastic sheet material of the enclosure may differ to accommodate devices other than a briefcase. For example, the amount of flexible plastic sheet material of the enclosure may be greater than 1080 square inches or less than 360 square inches or any other size to effectively accommodate different devices. In yet another embodiment, the bag portion of the enclosure has two corners opposite the opening of the enclosure and the corners may be pleated to accommodate the enclosure of bulkier devices such as purses and satchels.

In one novel method of use, the enclosure is prepared for use by enlarging the opening of the enclosure to allow a device such as a cellular phone to pass through the opening of the enclosure. In a subsequent step, the cellular phone or other device is placed in the enclosure, and is then transported into an operating room. While in the operating room, the cellular phone is still in the enclosure. The enclosure is then removed from the operating room and the cellular phone or other device is removed from the enclosure. In a final step, the enclosure is disposed of by the user. By removing the enclosure in the final step, the environment outside the operating room is protected from the contaminants transferred to the surface of the enclosure while the enclosure was within the operating room.

In other embodiments the use of these novel enclosures is not confined to operating rooms. The enclosures may be used to transport devices into intensive care units or neonatal care areas of hospitals. Other novel methods of use include those associated with semiconductor fabrication plants or in residences of individuals with compromised immune systems. One other novel method of use involves using the enclosures to bring devices into and out of homes or rooms of individuals who are extremely neat or are inflicted with various types of obsessive-compulsive disorders.

Further details and embodiments and techniques are described in the detailed description below. This summary does not purport to define the invention. The invention is defined by the claims.

BRIEF DESCRIPTION OF THE DRAWINGS

The accompanying drawings, where like numerals indicate like components, illustrate embodiments of the invention.

DETAILED DESCRIPTION

Reference will now be made in detail to some embodiments of the invention, examples of which are illustrated in the accompanying drawings.

Figure 1:
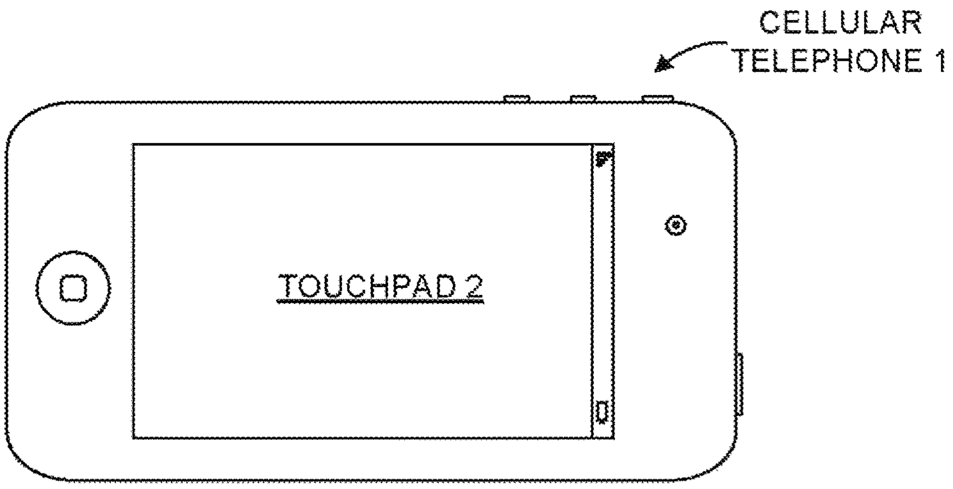
Fig. 1 (PRIOR ART)
FIG. 1 (Prior Art) is a drawing of a cellular telephone.
Figure 2:
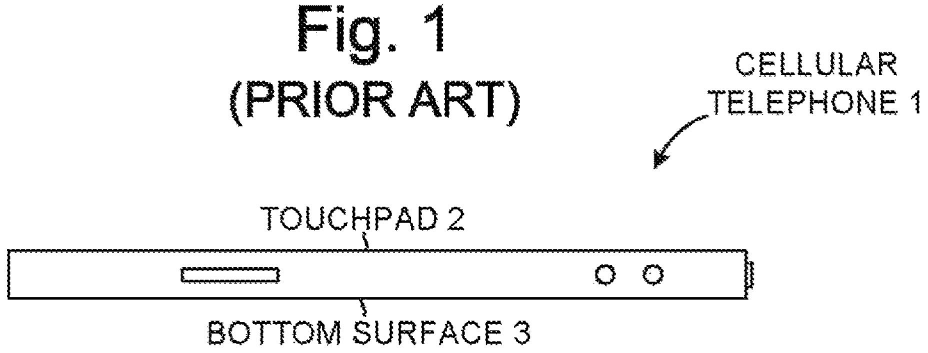
Fig. 2 (PRIOR ART)
FIG. 2 (Prior Art) is a side-view drawing of the cellular telephone of FIG. 1.
Figure 3:
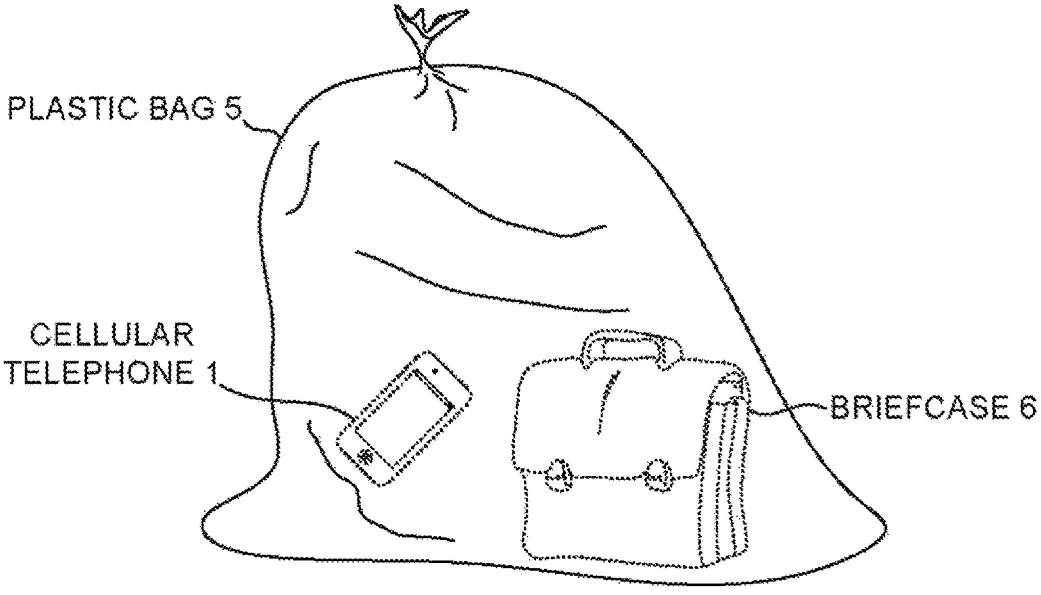
Fig. 3 (PRIOR ART)
FIG. 3 (Prior Art) is a drawing of a plastic bag containing a cellular phone and a briefcase.
Figure 4:
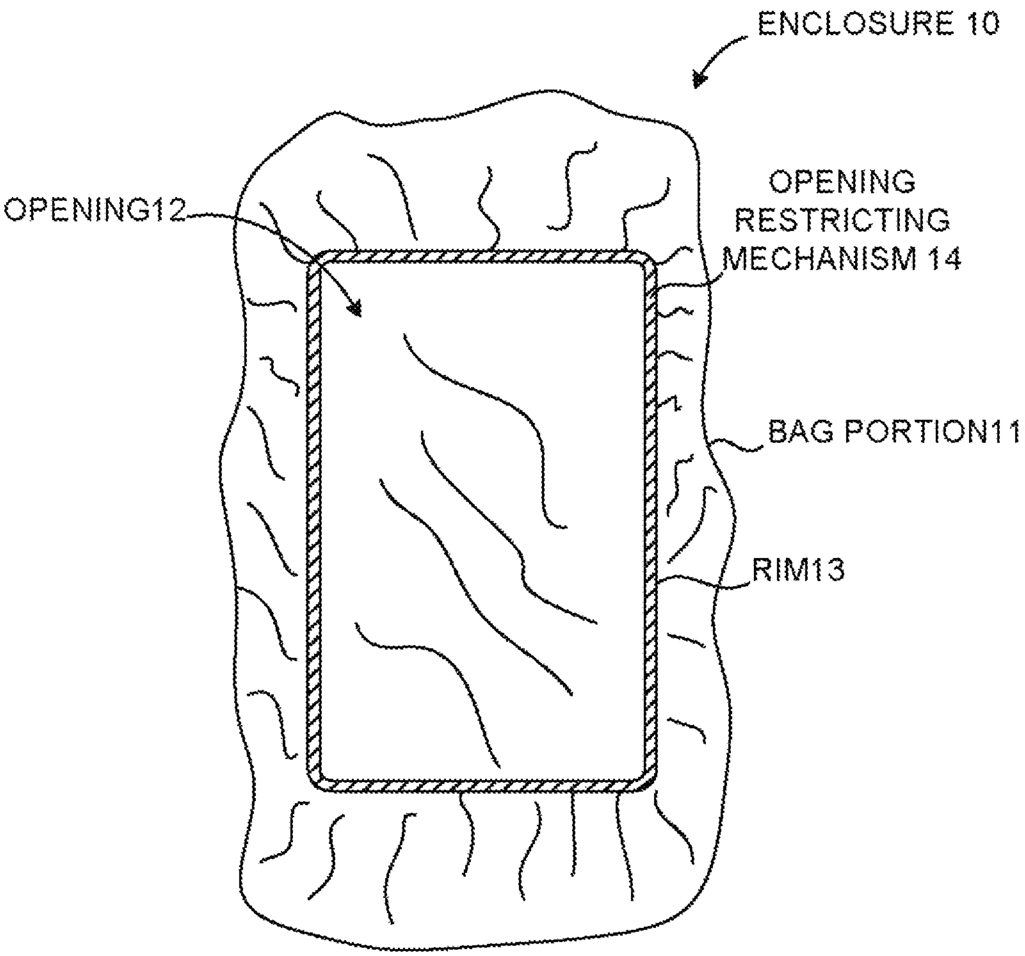
FIG. 4 is a drawing of an enclosure in accordance with one novel aspect.

FIG. 4 is a drawing of an enclosure 10 in accordance with one novel embodiment. Enclosure 10 has a bag portion 11, an opening 12, a rim 13, and an opening restricting mechanism 14. The opening 12 of bag portion 11 is defined by rim 13 at the periphery of bag portion 11. The opening restricting mechanism 14 is disposed along the rim 13 of opening 12 of bag portion 11. The opening restricting mechanism 14 in the novel embodiment of FIG. 4 is an elastic band. The elastic band provides for enlarging or reducing the size of opening 12 of bag portion 11. In other embodiments, the opening restricting mechanism 14 includes a drawstring or another suitable mechanism that provides for the enlargement or reduction of opening 12 of bag portion 11.

Bag portion 11 is made of a flexible plastic sheet material. The flexible plastic sheet material may be a single-layer sheet, or may include multiple layers, or may include multiple layers that are laminated together. Some layers may be porous whereas other layers may be nonporous. In one embodiment, the thickness of the flexible plastic sheet material is less than 10 mils, and may be between 0.10 mils and 1.2 mils in thickness. The flexible plastic sheet material is a nonporous material that may be disinfected with a medical grade disinfectant and may be spray coated with an antimicrobial material. The preferred embodiment of the enclosure is inexpensively manufactured and is disposable. In one embodiment the flexible plastic sheet material includes a polyethylene material. The polyethlyene material has a density and may be of a density between 0.900 to 0.965 grams per cubic centimeter. In another embodiments, the flexible plastic sheet material may include a poly vinyl chloride (PVC) material, a fluorinated hydrocarbon polymer material, a polytetrafluoroethylene (PTFE) material, a silicone rubber material, a nylon material, a flexible silicone composition, a polyamide material, a polyether block amide material, or a polypropylene material, or any other sheet material that is flexible and may be disinfected to reduce or eliminate infectious agents.

The flexible plastic sheet material may be manufactured by a blown-film production process or similar process for creating flexible plastic sheet material. In a blown-film production process, a polyethene or similar material is melted and extruded through an annular slit die, usually, vertically to form a thin walled tube. Air is then introduced via a hole in the center of the die to blow the tube causing it to expand and form a bubble. Mounted upon the top of the die, a high speed air ring blows onto the hot film to cool it. The tube of film is then passed through rolls where it is flattened to create the flexible plastic sheet material. This material can then be made into bag portions by sealing the flexible plastic sheet material across the width of the plastic sheet material and then cutting or perforating the plastic sheet material to make each bag portion.

In one example, the size of bag portion 11 is selected to accommodate different devices that may be transported into a medical environment. These devices may include, among other objects, cellular telephones, laptop computers, tablet computers, purses, satchels or briefcases. In one embodiment, the size of bag portion 11 is determined by the amount of flexible plastic sheet portion that bag portion 11 includes and that amount of flexible plastic sheet portion is more than eight square inches and is less than forty square inches. An enclosure with a bag portion including an amount of flexible plastic sheet portion that is more than eight square inches and is less than forty square inches may be used to enclose a cellular telephone.

Figure 5:
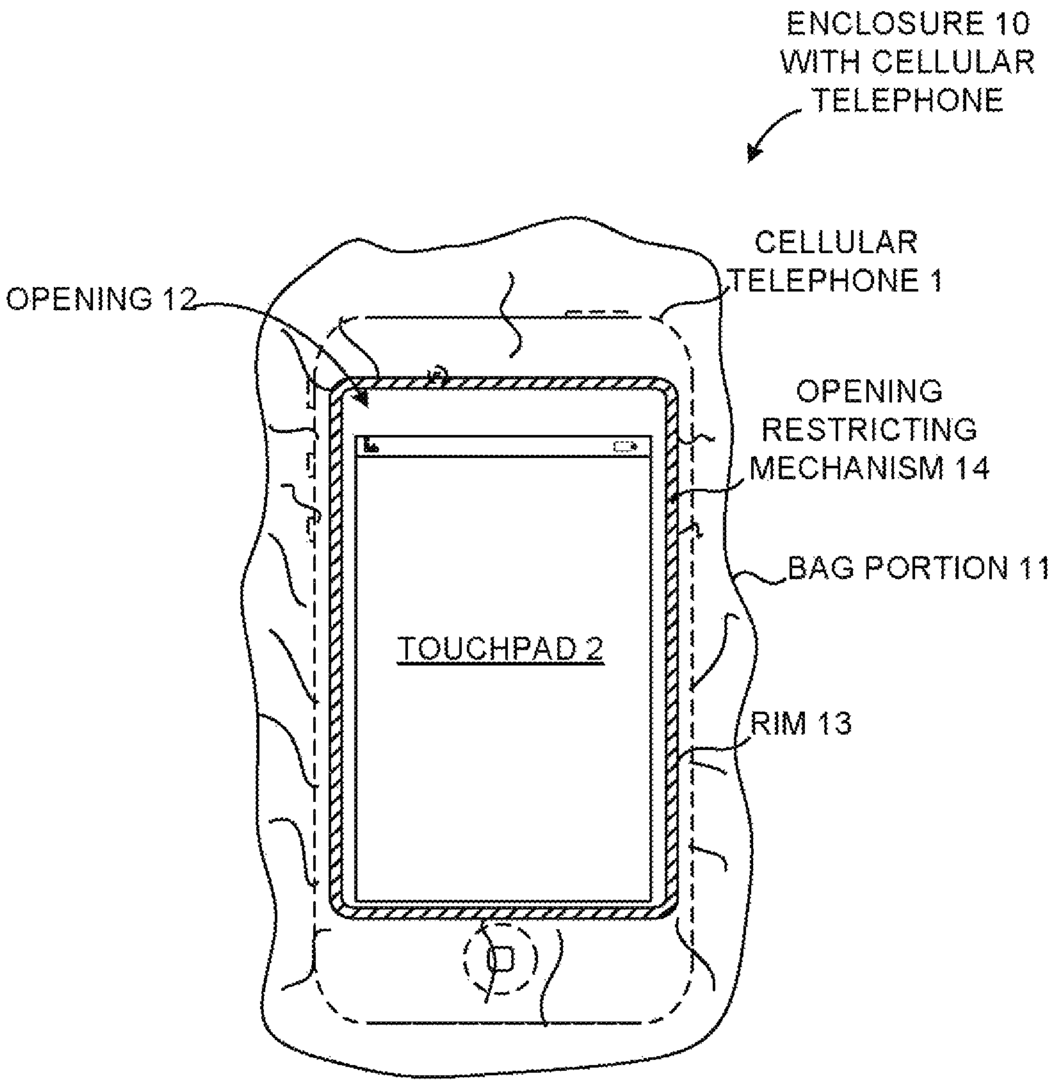
FIG. 5 is a drawing of an enclosure wherein a cellular telephone is disposed within the enclosure.

FIG. 5 is a drawing of the enclosure 10 of FIG. 4 enclosing a cellular telephone 1. The enclosure 10 includes the bag portion 11, the opening 12, the rim 13 and the opening restricting mechanism 14. In this embodiment, the opening restricting mechanism 14 is an elastic band. Cellular telephone 1 has a touchpad 2 and the opening 12 of enclosure 10 is shown positioned around the periphery of the surface of touchpad 2. In order for enclosure 10 to enclose cellular telephone 1, the opening is enlarged an amount to allow cellular phone 1 to pass into opening 12 of enclosure 10. After the cellular phone is disposed within enclosure 10, the opening restricting mechanism is used to reduce the opening 12 such that all surfaces of cellular telephone 1 are enclosed by enclosure 10 except for the touchpad 2. Touchpad 2 is still able to be accessed by a medical professional or other user of cellular telephone 1. Preferably, the area of the opening 12 when the cellular telephone 1 is in place in the enclosure 10 is at least six square inches so that the touchpad 2 can be manipulated through the opening.

In another embodiment, the opening restricting mechanism 14 reduces the opening 12 of enclosure 10 such that all surfaces of cellular telephone 1 are enclosed by bag portion 11 including the surface of touchpad 2. In some embodiments, the flexible plastic sheet portion of bag portion 11 is transparent and allows medical professionals or other users to see and access the control buttons of cellular telephone 1 within enclosure 10. In this manner, a medical professional or other user could control the volume, connect or disconnect calls, or control other functions of the cellular telephone by using the control buttons of cellular telephone 1 while the device is within transparent enclosure 10. In other novel embodiments, the enclosure 10 has an opening or several openings that extend through bag portion 11 to accommodate wires used for power connections, earphone and mouthpiece connections, or other similar type of connecting wires. These openings in bag portion 11 may be specifically located to accommodate connecting wire connections of popular smartphones, tablet or laptop computers, or other electronic devices. For example, a first opening is located in one side of the bag portion to accommodate a cord to a headphones, and a second opening is located in an opposite side of the bag portion to accommodate a cord to a AC-to-DC wall adapter. In other novel embodiments still, the bag portion 11 includes fitted bottoms and/or sides to closely conform to the shape of devices such as smartphones, tablet or laptop computers, or other electronic devices. In these or other embodiments the bag portion 11 may be constructed of an amount of flexible plastic sheet portion that causes the bag portion 11 to enclose a smartphone, tablet or laptop computer, or other electronic device in a snug or tight fitting manner. In one particular embodiment, the bag portion 11 contains an additional pocket structure on an exterior surface of bag portion 11. When the enclosure is provided to the user, this pocket structure includes an alcohol or other type of disinfecting wipe. The alcohol or other disinfecting wipe can also be attached to the bag portion 11 by an adhesive patch, hook and loop fasteners, or in any other similar manner.

In some novel embodiments, the flexible plastic sheet portion of bag portion 11 of enclosure 10 includes an effective amount of an antibacterial material, an antifungal material, or an antiviral material, or mixtures thereof. By including an effective amount of an antibacterial material into the flexible plastic sheet material of bag portion 11 of the enclosure 10, the enclosure 10 may have antibacterial properties sufficient to prevent or reduce the likelihood of infectious agents present on the surfaces of enclosure 10 and also may reduce the likeliness of health-care-associated infections. In one aspect, the antibacterial compound may be gentamycin, clindamycin, or vancomycin or the antibacterial compound may be selected from the group including an aminoglycoside, a lincosamide, a glycopeptide, or mixtures thereof. In other embodiments, other effective antibacterial materials or mixtures thereof are used. In one embodiment, the effective amount of antibacterial material is 0.0001 percent to 5.0 percent by weight of the flexible plastic sheet material. Similarly, if the flexible plastic sheet material of bag portion 11 of enclosure 10 includes an effective amount of an antifungal material in the flexible plastic sheet portion of bag portion 11 of the enclosure 10, the enclosure 10 may have antifungal properties sufficient to prevent or reduce the likelihood of infectious agents present on the surfaces of enclosure 10 and also may reduce the likeliness and occurrence of health-care-associated infections. In one aspect, the antifungal material may be amphotericin B or a compound selected from the group including: a polyene, an azole, an allylamine, a morpholine, a glucan synthesis inhibitor, a systemic agent, an antimetabolite or mixtures thereof. The effective amount of antifungal material may be an amount that is 0.0001 percent to 5.0 percent by weight of the flexible plastic sheet material. In other embodiments, other effective antifungal materials or mixtures thereof are used. If the flexible plastic sheet material of bag portion 11 of enclosure 10 includes an effective amount of an antiviral material in the flexible plastic sheet portion of bag portion 11 of the enclosure 10, the enclosure 10 may have antiviral properties sufficient to prevent or reduce the likelihood of infectious agents present on the surfaces of enclosure 10 and also may reduce the likeliness of health-care-associated infections. In one aspect the antiviral material may be acyclovir or a compound selected from the group including a xanthate compound, gancyclovir, dichloromethane, ethylene vinyl acetate or mixtures thereof. The effective amount of antiviral material may be an amount that is 0.0001 percent to 10.0 percent by weight of the of the flexible plastic sheet material. In other embodiments, other effective antiviral compounds or mixtures thereof are used. To combine the plastic material of the plastic sheet portion with either an antibiotic material, an antifungal material, or an antiviral material, or mixtures thereof, the precursor plastic material should be mixed with the antibiotic, antifungal, or antiviral materials, and then brought to a molten stage. Other methods of combining similar compounds are well known in the art and can be used to combine or impregnate the plastic sheet material with antibiotic, antifungal, or antiviral materials or mixtures thereof. Where the flexible plastic sheet material is a fibrous and porous material, or where it includes a fibrous and porous constituent layer, the fibrous and porous material may be made to retain an amount of an antimicrobial material. An antimicrobial material can also be provided as part of the flexible plastic sheet material by coating the antimicrobial material onto a plastic sheet layer to form an antimicrobial layer of the overall flexible plastic sheet material.

Figure 6:
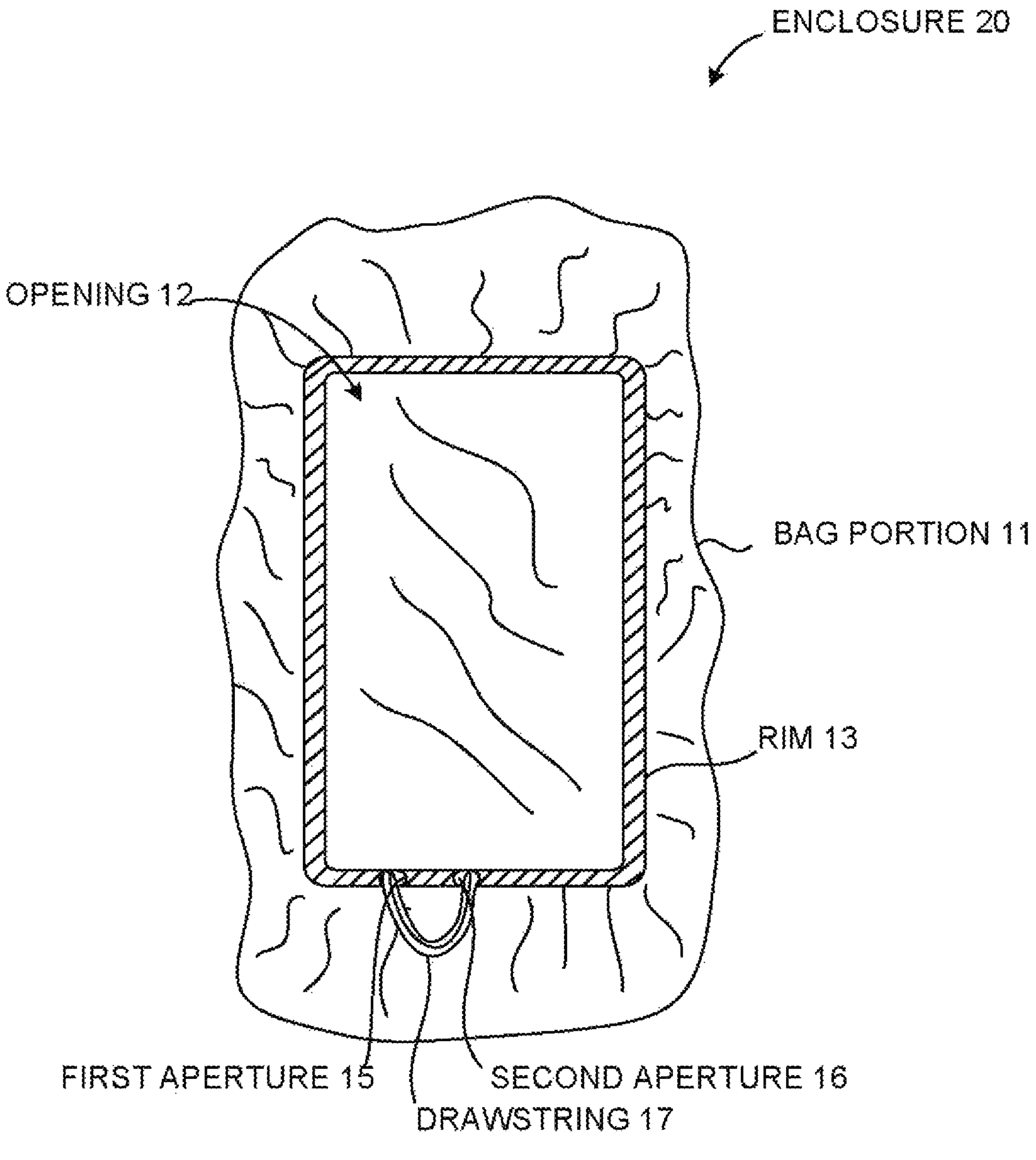
FIG. 6 is a drawing of an enclosure in accordance with a second novel aspect.

FIG. 6 is a drawing of an enclosure 20 in accordance with one novel aspect. The enclosure 20 has a bag portion 11, an opening 12, a rim 13 and an opening restricting mechanism. In this embodiment, the opening restricting mechanism is a drawstring 17. The rim 13 of enclosure 20 is hollow and includes a first aperture 15 and a second aperture 16. Drawstring 17 passes through first aperture 15, into the hollow rim 13, and through second aperture 16. By pulling an amount of drawstring out of both apertures, the opening 12 is reduced in size. To enlarge opening 12, the rim 13 is pulled such to pull a larger amount of drawstring 17 through first aperture 15 and second aperture 16 and into rim 13. In another embodiment, drawstring 17 extends from rim 13 through only one aperture for the purpose of enlarging and reducing the size of opening 12.

Figure 7:
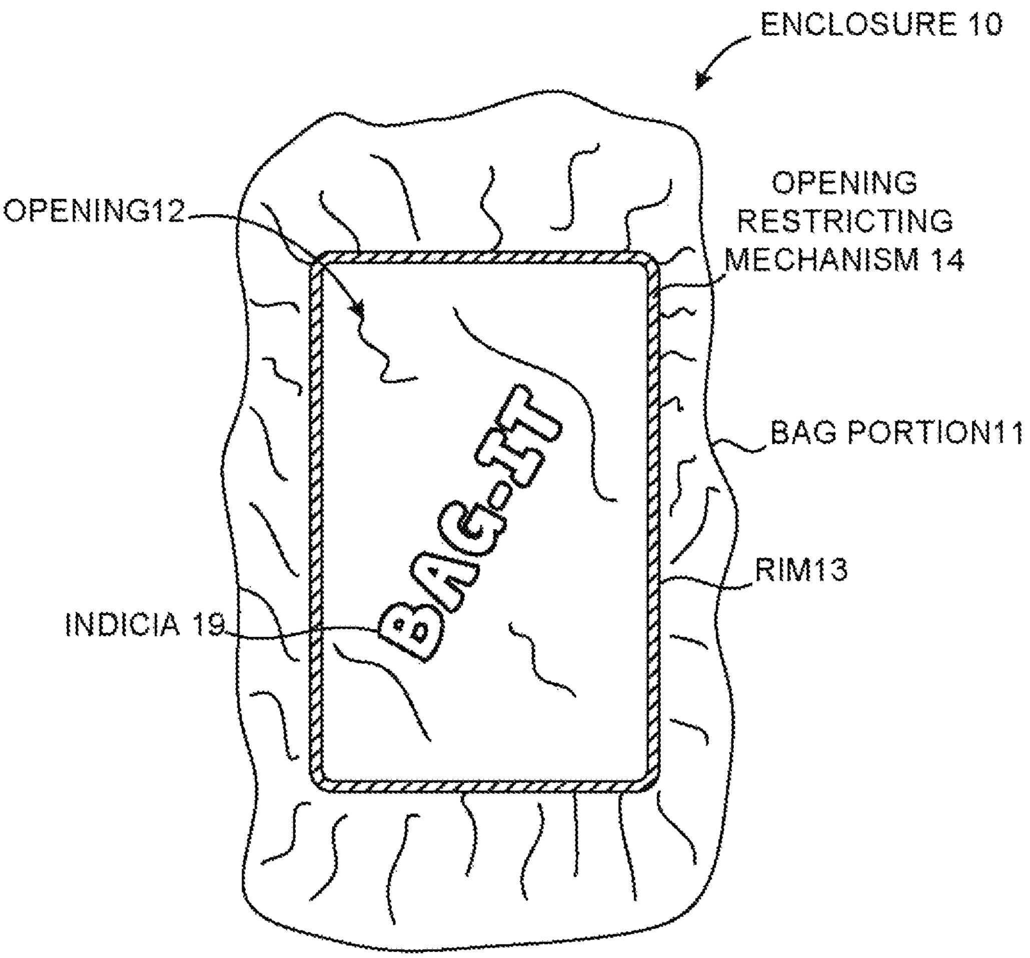
FIG. 7 is a drawing of an enclosure with indicia in accordance with another novel aspect.

FIG. 7 is a drawing of the enclosure 10 of FIG. 4. in accordance with another novel embodiment. The enclosure 10 of FIG. 4 includes bag portion 11 with rim 13, opening 12, opening restricting mechanism 14 and indicia 19. Indicia 19 may include the trade name of enclosure 20, operating instructions, advertising, or other indicia. The indicia 19 may be placed on enclosure 20 by ink-jet printing, silk-screening, or any other type of printing method suitable for the printing of flexible plastic sheet materials. The indicia 19 may be placed on the inside, outside, and or any surface of the enclosure.

Figure 8:
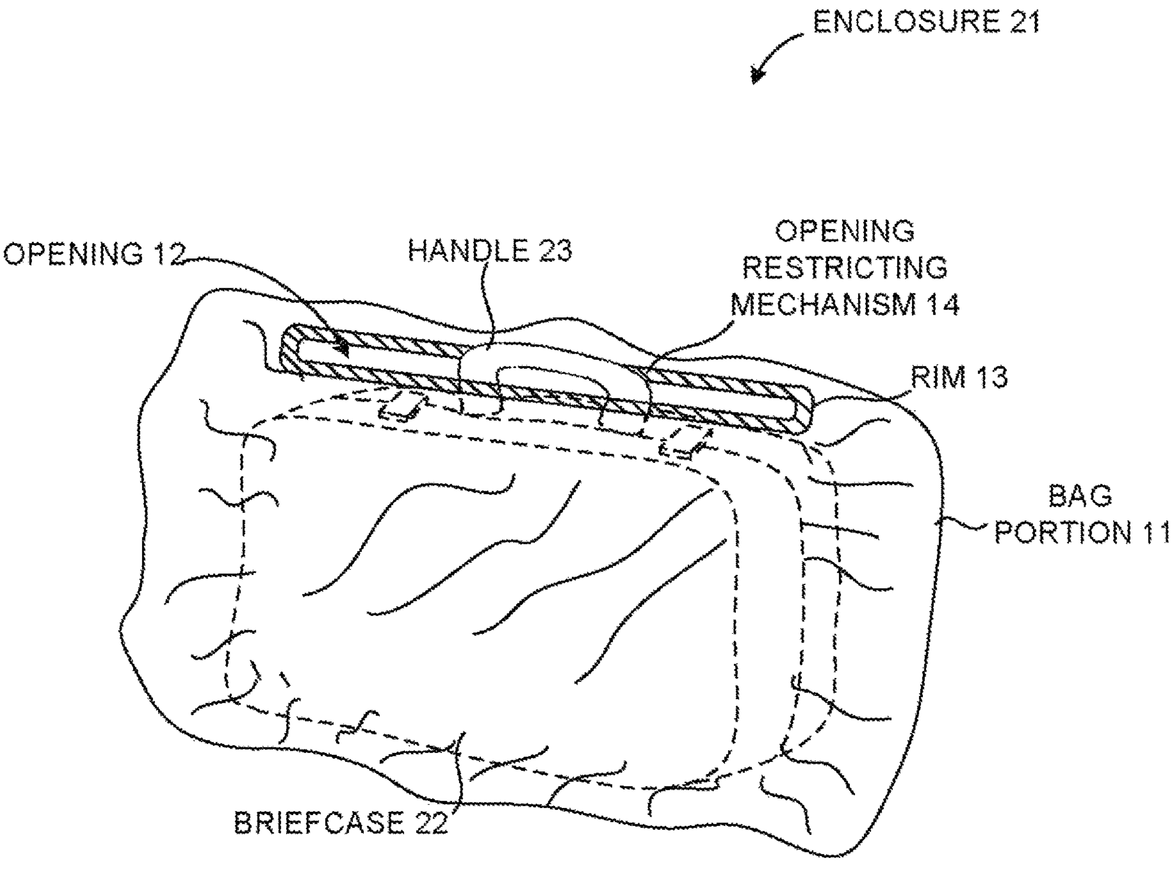
FIG. 8 is a drawing of an enclosure wherein a briefcase has been placed within the enclosure.

FIG. 8 is a drawing of an enclosure 21 that is enclosing a briefcase 22 with a handle 23. Enclosure 21 includes a bag portion 11 with a rim 13 and an opening 12 and opening restricting mechanism 14. In this embodiment of FIG. 8, the opening restricting mechanism is an elastic band. The opening restricting mechanism may differ in alternative embodiments and may include a drawstring or other suitable apparatus for reducing or enlarging the size of opening 12 of bag portion 11. Bag portion 11 includes a flexible plastic sheet portion and the flexible plastic sheet portion is in an amount greater than 360 square inches and less than an amount of 1080 square inches. The flexible plastic sheet material of bag portion 11 also has a thickness of less than 10 mils and the thickness may be between 0.10 mils and 1.2 mils thick. In one embodiment the flexible plastic sheet material is a nonporous material that may be disinfected with a medical grade disinfectant. The enclosure 21 of FIG. 8 shows handle 23 of briefcase 22 extending through opening 12 of enclosure 21. In this embodiment, the briefcase 22 with enclosure 21 can be easily carried by a healthcare professional or other user. The healthcare professional can also open the briefcase 22 through the opening without removing briefcase 22 from enclosure 21. In this manner, the healthcare professional or other user can access the contents of the case with minimal or no contact with the contaminated outer surfaces of briefcase 22. In another embodiment, the bag portion 11 may be transparent. In yet another embodiment, the briefcase 22 and handle 23 may be entirely disposed within enclosure 21. In still other embodiments, the amount of flexible plastic sheet material of bag portion 11 may differ to accommodate devices other than a briefcase. These devices may include a laptop computer, a tablet computer, a purse, a satchel or any other type of device that a healthcare professional or other user may desire to transport into a medical environment. For example, the amount of plastic sheet material in bag portion 11 may be greater than 1080 square inches or less than 360 square inches or any other size to effectively accommodate different devices. In other embodiments, bag portion 11 has two corners opposite opening 12 and the two corners opposite opening 12 of the bag portion 11 may be pleated to accommodate the enclosure of bulkier devices such as purses and satchels.

Figure 9:
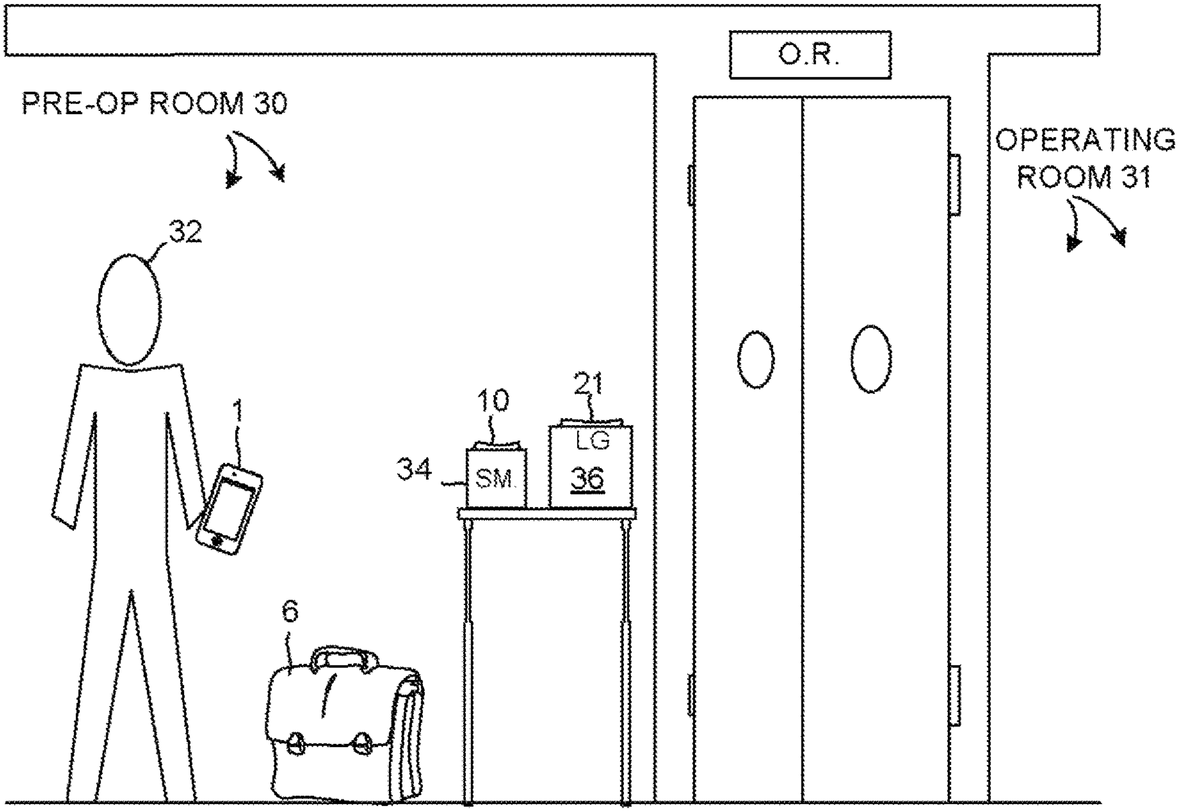
FIG. 9 is a drawing of a healthcare professional in a pre-op room preparing for entrance into an operating room. Multiple dispensers containing enclosures are located in the pre-op room.

FIG. 9 is a drawing showing a healthcare professional 32 in a pre-op room 30 preparing to enter an operating room 31 with a cellular telephone 1 and a briefcase 6. Healthcare professional 32 is in pre-op room 30 and will enter operating room 31 after the healthcare professional 32 has disinfected their person and protected the cellular telephone 1 and briefcase 6 from causing health-care-associated infections. Pre-op room 30 includes a first enclosure 10 extending from a first dispenser 34 and a second enclosure 21 extending from a second dispenser 36. First enclosure 10 is the enclosure of FIG. 4 and has a bag portion 11 with an opening 12, a rim portion 13, and an opening restricting mechanism 14 (not shown). Bag portion 11 of enclosure 21 includes a flexible plastic sheet portion that is in an amount greater than eight square inches and an amount less than forty square inches. First dispenser 34 includes a plurality of enclosures, an opening, and a mechanism allowing for a subsequent enclosure to be disposed at the opening of dispenser 34 after the first enclosure 10 has been pulled from dispenser 34 through the opening of dispenser 34. Dispenser 34 protects the plurality of enclosures from infectious agents while the enclosures are disposed within dispenser 34. The healthcare professional 32 removes the enclosure 10 from dispenser 34 and uses it to enclose cellular telephone 1. Second enclosure 21 is the enclosure of FIG. 8 and has a bag portion 11 with an opening 12, a rim portion 13, and an opening restricting mechanism 14 (not shown). Bag portion 11 of enclosure 21 includes a flexible plastic sheet portion that is in an amount greater than 360 square inches and an amount less than 1080 square inches. Second dispenser 36 includes a plurality of enclosures, an opening, and a mechanism allowing for a subsequent enclosure to be disposed at the opening of dispenser 36 after a first enclosure has been pulled from dispenser 36 through the opening of dispenser 36. Dispenser 36 protects the plurality of enclosures from infectious agents while the enclosures are disposed within dispenser 36. The healthcare professional 32 removes the enclosure 21 from dispenser 36 and uses it to enclose briefcase 6 before entering disinfected operating room 31. In some embodiments the dispensers 34 and 36 are simply boxes or cartons containing the enclosures. Multiple different sizes of disposable enclosures are provided in the same place immediately adjacent the entrance to the operating room 31 in this fashion.

Figure 10:
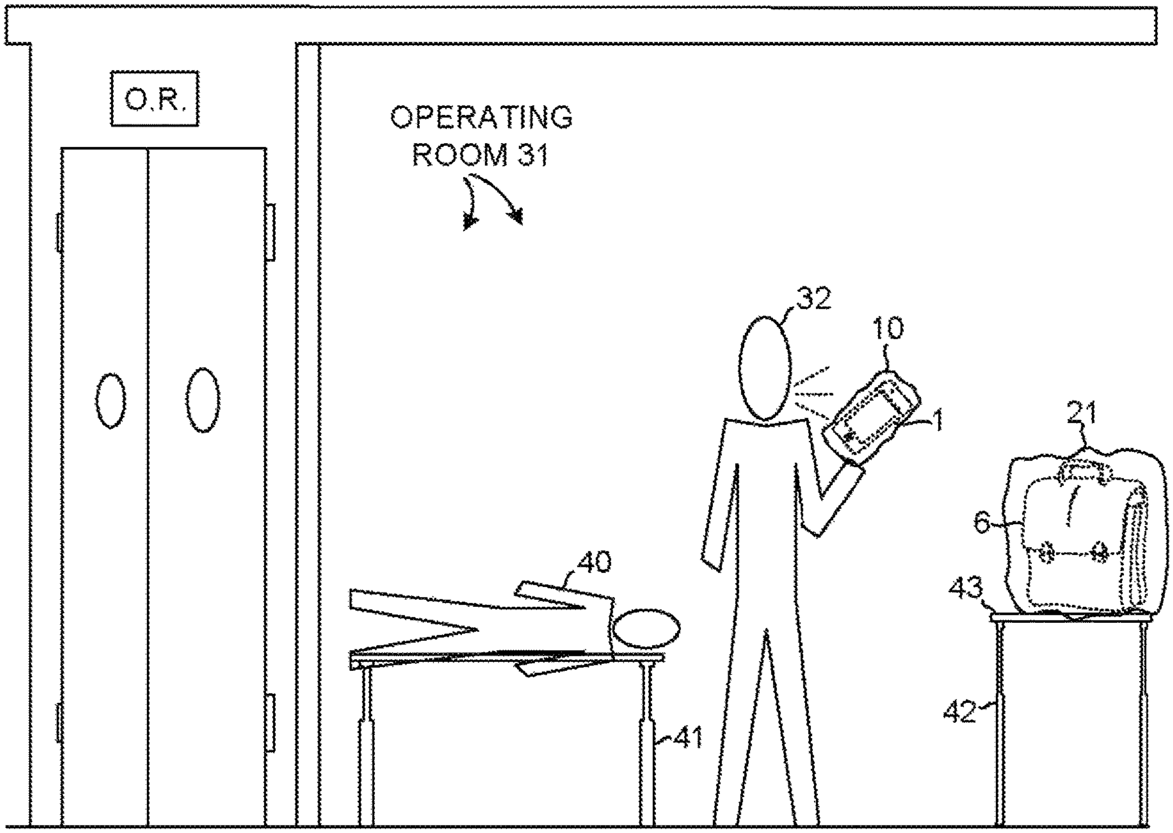
FIG. 10 is a drawing of a healthcare professional in an operating room using a cellular telephone that has been placed within an enclosure.

FIG. 10 is a drawing of an operating room 31 showing the healthcare professional 32 of FIG. 9 after leaving the pre-op room 30 and upon entered the operating room 31. Operating room 31 includes a patient 40 on an operating table 41 and table 42 with a surface 43. Healthcare professional 32 is shown using a cellular phone 1 disposed within an enclosure 10. Also shown is the briefcase 6 of FIG. 9 after it has been disposed within an enclosure 21. The healthcare professional 32 has placed briefcase 6 and enclosure 21 on surface 43 of table 42. Healthcare professional 32 may be using the cellular telephone 1 to contact experts on procedures necessary for patient 40. After using the cellular phone 1, the healthcare professional may place the cellular phone on a surface of operating table 41, surface 43 of table 42 or any other location in operating room 31. Enclosures 10 and 21 prevent any infectious agents present on surfaces of cellular telephone 1 or briefcase 6, respectively from contaminating surface 43 or any other surface in operating room 31. The healthcare professional 32 may also be required to access information within briefcase 6 while it is enclosed within enclosure 21. While in the operating room, the surfaces of enclosures 10 and 21 may become contaminated with infectious agents from patient 40 or from other sources of infectious agents. In order to prevent contamination of the pre-op room 30 of FIG. 9 or other areas, the healthcare professional 32 will remove cellular telephone 1 from enclosure 10, and will remove briefcase 6 from enclosure 21, and will immediately dispose of enclosures 10 and 21 after leaving operating room 31. In another embodiment, healthcare professional 32 will remove the devices and dispose of enclosures 10 and 21 immediately before leaving operating room 31. In yet other embodiments, enclosures 10 and 21 may be wiped with disinfectants while in the operating room or the enclosures 10 and 21 may be removed and replaced with newly dispensed enclosures in the operating room. In this latter embodiment, dispensers of enclosures would be located in the operating room and could be used to dispense enclosures every time a new patient is brought into the operating room.

Figure 11:
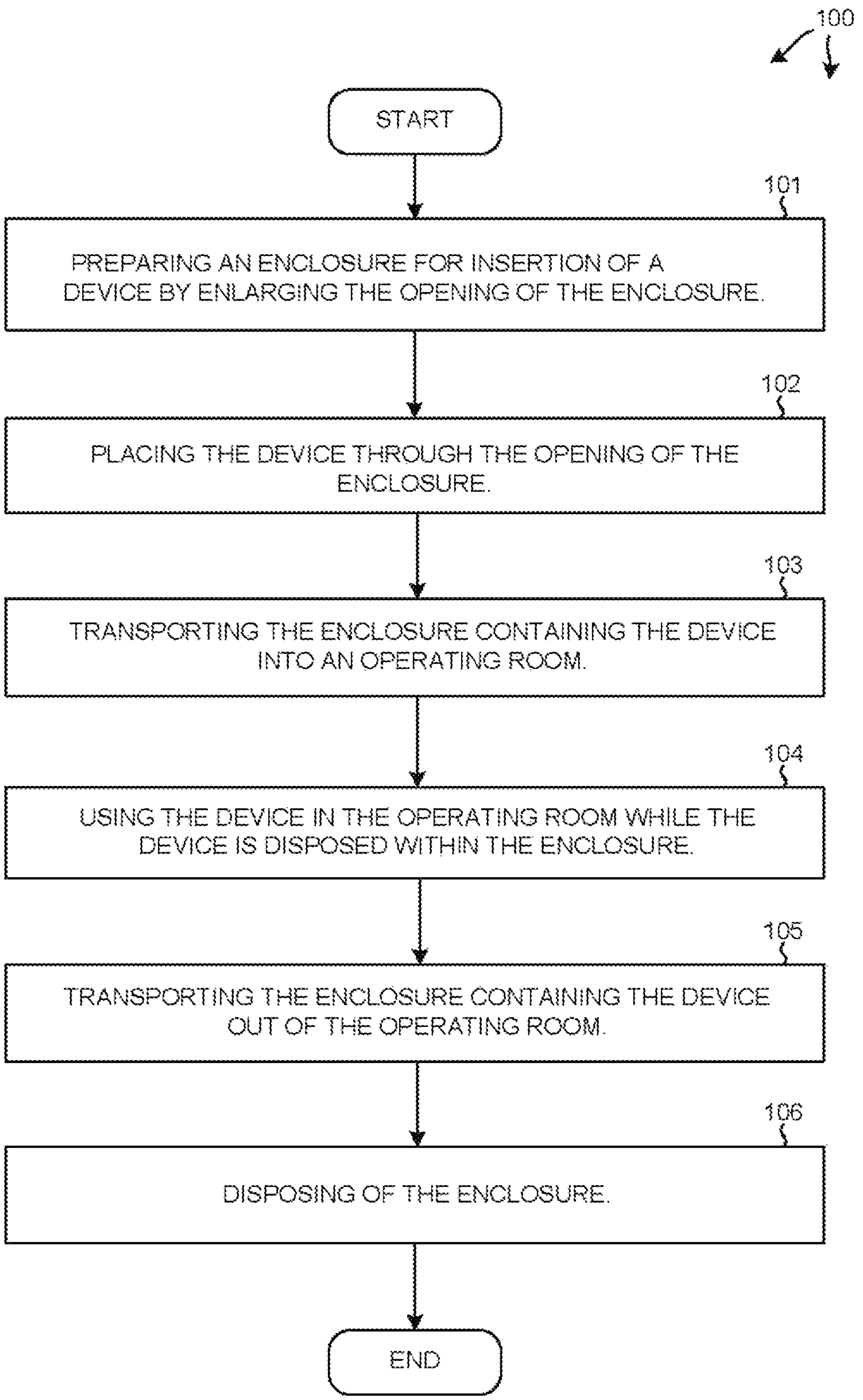
FIG. 11 is a flowchart of a novel method of use of an enclosure to prevent health-care-associated infections caused by contaminated devices.

FIG. 11 is a flowchart showing a novel method 100 of using an enclosure to prevent health-care-associated infections caused by contaminated devices. In a first step 101 an enclosure has a bag portion 11 with an opening 12 and an opening restriction mechanism 14 (not shown) and the opening restriction mechanism is used to enlarge the opening of the enclosure for insertion of device such as a cellular telephone. In a second step 102, the device is moved through the opening of the enclosure and positioned within the enclosure. In a third step 103, the enclosure and cellular telephone are transported into an operating room. In a fourth step 104 of this novel method, the device is used while the device is within the enclosure and while in the operating room. In a fifth step 105, the device is transported out of the operating room while still within the enclosure and in a final step 106, the device is removed from the enclosure and the enclosure is disposed of by the healthcare professional or other user. In another novel method, an additional step of wiping the enclosure with a disinfectant after the patient has been treated and before another patient is brought into the operating room. In yet another novel method, the enclosure is removed in between patients and is replaced with another enclosure before a new patient is brought into the operating room.

Figure 12:
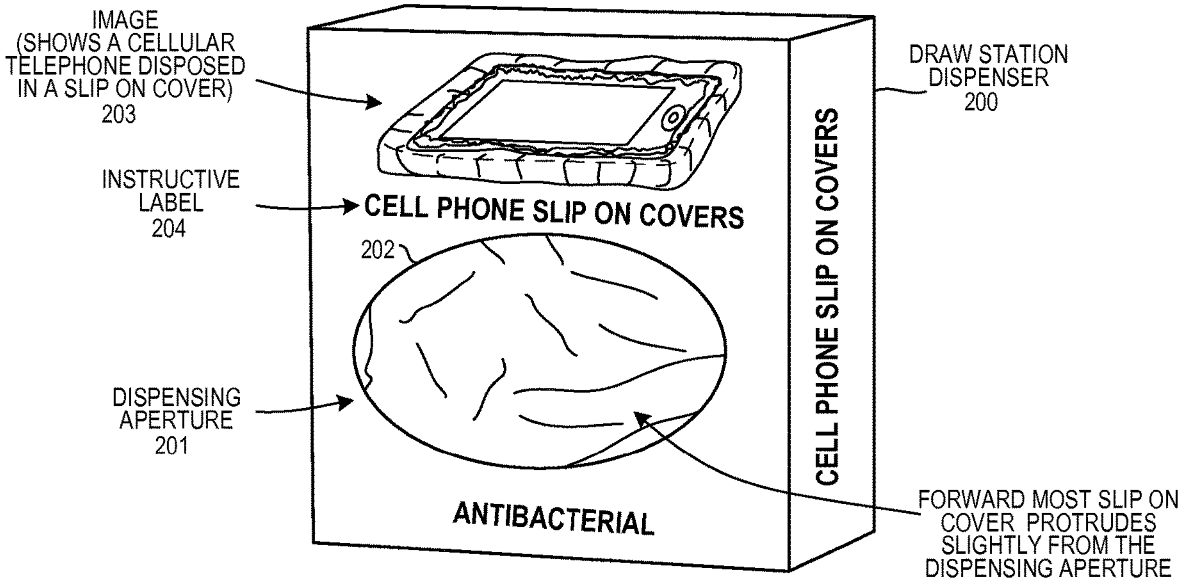
FIG. 12 is a perspective diagram of a draw station dispenser that dispenses cell phone slip on covers (enclosures) in accordance with another novel aspect.

FIG. 12 is a diagram of a draw station dispenser 200 in accordance with another novel aspect. The dispenser is a box having a dispensing aperture 201. The dispensing aperture may be formed by tearing a perforated edge 202 in the case where the box of the dispenser is an inexpensive cardboard box. Multiple enclosures of the type described above for attachment to a cellular telephone are disposed in the dispenser 200 such that the forward most enclosure protrudes slightly from the dispensing aperture 201 as shown in FIG. 12. The enclosures in this example are also referred to as "slip on covers". In addition to the dispensing aperture, the dispenser 200 bears an image 203. The image 203, which may be a photographic image or an illustration, shows a cellular telephone disposed in a slip on cover such that the rim of the opening in the slip on cover is located over the touch pad of the cellular telephone as shown. The touchpad of the cellular telephone is exposed through the opening, and can be manipulated manually through the opening. An elastic band in the rim of the slip on cover is shown pulling the flexible plastic sheet material of the slip on cover to be somewhat tight against the side surfaces and the bottom surface of the cellular telephone. In addition, the dispenser 200 contains an instructive label 204. The instructive label 204, which in this case says "CELL PHONE SLIP ON COVERS", indicates that the slip on covers are to be placed on cellular telephones. With the dispenser 200, the slip on covers are folded or nested so that individual slip on covers can be extracted from the dispensing aperture one at a time, and as each individual slip on cover is removed, a part of the next slip on cover is left protruding from the dispensing aperture. The dispenser 200 is typically placed in a pre-op room or locker room or other place where medical professionals are provided with disposable shoe covers, disposable hair caps, disposable masks, disposable surgical gloves, and other disposable clothing just prior to entering an operating room.

A user (for example, a health care professional) removes a slip on cover 205 from the dispenser 200, and places the slip on cover over a cellular telephone 206 such that the opening is situated over the touchpad 208 of the cellular telephone 206 as illustrated in the image on the dispenser. The cellular telephone 206 may be placed directly into the slip on cover, or the cellular telephone 206 may already be disposed in another form fitting-cover so that the combination of the cellular telephone and its form-fitting cover is placed into the slip on cover. In one example, the placing of the cellular telephone 206 into the slip on cover 205 involves expanding the opening against a restricting force of the elastic band 207, and then moving the cellular telephone 206 through the expanded opening, and then allowing the elastic band 207 to restrict the size of the opening when the cellular telephone is disposed in the slip on cover.

Figure 13:
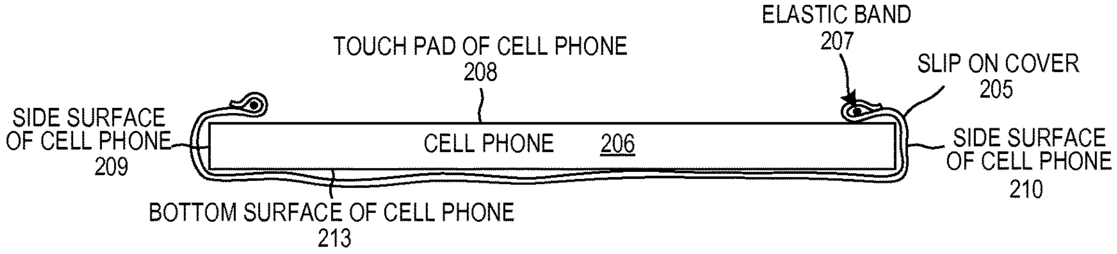
FIG. 13 is a lengthwise cross-sectional side view of a cellular telephone disposed in a cell phone slip on cover (enclosure) that has been extracted from the dispenser of FIG. 12.
Figure 14:
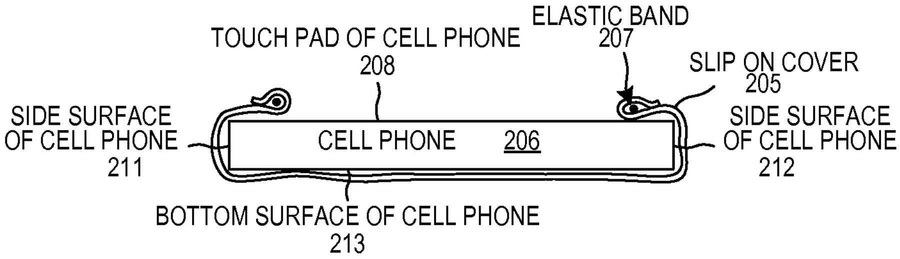
FIG. 14 is a widthwise cross-sectional side view of a cellular telephone of FIG. 13.
Figure 15:
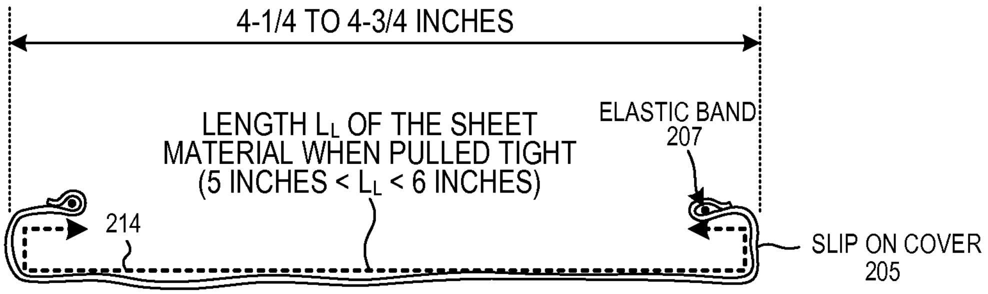
FIG. 15 is a diagram that shows the length $L_L$ of the flexible sheet material of the slip on cover (enclosure) that covers the cellular telephone of FIG. 13.
Figure 16:
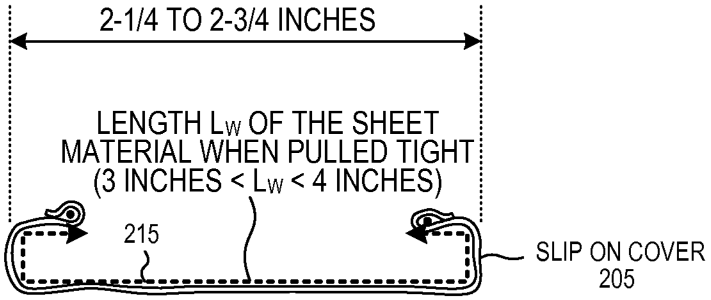
FIG. 16 is a diagram that shows the length $L_W$ of the flexible sheet material of the slip on cover (enclosure) that covers the cellular telephone of FIG. 13.

FIG. 13 is a lengthwise cross-sectional side view of the cellular telephone 206 in the slip on cover 205 in this particular example. FIG. 14 is a widthwise cross-sectional side view of the cellular telephone 206 in the slip on cover 205. The slip on cover 205 covers at least a majority of the area of the touchpad 208. The flexible plastic sheet material covers the four side surface 209-212 of the cellular telephone 206, and also covers the bottom surface 213 of the cellular telephone 206 as shown. In this specific example, the slip on cover 205 is of a specific size, and accommodates in a desirable fashion, either a cellular telephone without a fitted cover or a cellular telephone in its fitted cover. As shown in FIG. 15 by the dashed double headed arrow 214, the flexible plastic sheet material has a length $L_L$ measured from a first location on the rim on a side of the opening, extending lengthwise around the bottom surface of the cellular telephone, and to a second location on the rim on the opposite side of the opening. This length $L_L$ is more than five inches and less than six inches. As shown in FIG. 16 by the dashed double headed arrow 215, the flexible plastic sheet material has a length $L_W$ measured from a third location on the rim on a side of the opening, extending widthwise around the bottom surface of the cellular telephone, and to a fourth location on the rim on the opposite side of the opening. Length $L_W$ is more than three inches and less than four inches.

In one example, the bottom portion of the flexible plastic sheet material of the slip on cover 205 is of a substantially rectangular shape that is 4.25 to 4.75 inches long and 2.25 to 2.75 inches wide. This rectangular shape substantially matches the size of the bottom surface of the cellular telephone 213. The side portions of the flexible plastic sheet material of the slip on cover 205 are formed so that they substantially match the side surfaces of the cellular telephone 206. Accordingly, when the cellular telephone 206 is in place in the slip on cover 205, the edges of the rim take on the rough form of a rectangle and roughly parallel the edges of the rectangular top surface of the cellular telephone. The rim of the opening of the enclosure (when the enclosure is in place on the cellular telephone) has a substantially rectangular shape as pictured in the image 203 on the dispenser.

After the user has placed the cellular telephone 206 into the slip on cover 205, the cellular telephone 206 (when it is in its slip on cover 205) is carried by the user into an operating room.

Although the enclosure is described above in a specific example as having an opening with an elastic band or drawstring, other examples of the enclosure do not have elastic bands or drawstrings. In one example, the enclosure is a transparent plastic zip lock bag of a seamed construction just like a common commercially-available freezer bag (such as a Ziploc brand double zipper freezer bag available from SC Johnson & Son, Inc. of 1525 Howe Street, Racine, Wis.), except that the novel enclosure: 1) has a size of about 3.25 inches wide by about 6.0 inches long, and 2) has an opening about 2 inches wide by 3 inches long in the top panel of the plastic sheeting of the bag enclosure. The 3.25 inch dimension is the length of the zipper side of the bag enclosure that opens, and through which the cellular telephone can be introduced into the bag enclosure. The opening is positioned so that the opening will be over the touchpad of a cellular telephone when a cellular telephone of a standard size is disposed faceup in the bag enclosure. The opening may be a cutout formed by cutting a 2 inch by 3 inch rectangle out of the top panel of the bag enclosure after the bag enclosure has been otherwise manufactured, or the opening may be formed in a sheet of plastic material when the plastic sheeting is being folded cut and seamed during bag manufacture. A box of such baggie-type enclosures may be packaged in a dispensing cardboard box of the same type used by SC Johnson & Son, Inc. to package its ordinary ziploc brand freezer bags.

The use of these novel enclosures is not confined to operating rooms. In another novel embodiment, the enclosures may be used to transport devices into intensive care units or neonatal care units of hospitals. In yet another novel method, the enclosure is used to transport devices into a clean room of a semiconductor fabrication plant. One alternative method involves the use of enclosures to transport devices into environments of individuals with compromised immune systems. Another novel method involves using enclosures to bring devices into homes or rooms of those inflicted with compulsive disorders to both prevent stress and ease of treatment in those individuals.

Although certain specific embodiments are described above for instructional purposes, the teachings of this patent document have general applicability and are not limited to the specific embodiments described above. Accordingly, various modifications, adaptations, and combinations of various features of the described embodiments can be practiced without departing from the scope of the invention as set forth in the claims.

What is claimed is:

1. A method involving an enclosure, wherein the enclosure includes a bag portion and an opening restricting mechanism disposed along a rim of an opening of the bag portion, wherein the bag portion is made of an amount of flexible plastic sheet material, and wherein the amount is more than eight square inches and is less than forty square inches, the method comprising:

(a) enlarging the opening of the bag portion enough to allow a device to pass through the opening and into the bag portion of the enclosure, wherein the device is taken from the group consisting of: a cellular telephone, a laptop computer, and a tablet computer;

(b) placing the device through the opening and into the bag portion of the enclosure, wherein a portion of a touchpad or keyboard of the device is exposed to an outer environment through the opening;

(c) transporting the enclosure containing the device into an operating room;

(d) using the device in the operating room while the device is disposed in the enclosure, wherein the portion of the touchpad or keyboard of the device is directly accessible through the opening without contact of any intervening portion of the enclosure, and wherein at least part of the touchpad or keyboard of the device is usable by directly contacting the portion of the touchpad or keyboard of the device through the opening without contacting any interior of the enclosure while the device is disposed in the enclosure;

(e) transporting the enclosure containing the device out of the operating room; and (f) removing the device from the enclosure.

2. The method of claim 1, wherein the device is a telephone.

3. The method of claim 2, wherein the flexible plastic sheet material is transparent.

4. The method of claim 1, wherein the flexible plastic sheet material is taken from the group consisting of: a poly vinyl chloride (PVC) material, a polyethylene material, a polypropylene material, a fluorinated hydrocarbon polymer material, a polytetrafluoroethylene (PTFE) material, a silicone rubber material, a nylon material, a flexible silicone composition, a polyamide material, and a polyether block amide material.

5. The method of claim 1, wherein the flexible plastic sheet material comprises an antimicrobial material taken from the group consisting of: an antibacterial material, an antifungal material, and an antiviral material, and wherein the antimicrobial material protects the operating room from outside biological contaminants and protects an outside of the operating room from biological contaminants within the operating room.

6. The method of claim 5, wherein the antimicrobial material is about 0.0001 percent to about 5 percent by weight of the flexible plastic sheet material.

7. The method of claim 1, wherein step (b) further comprises placing the device through the opening and into the bag portion of the enclosure such that the portion of the device remains outside of the enclosure.

8. The method of claim 1, wherein the method also comprises:

(g) disposing of the enclosure.

9. The method of claim 1, wherein the using of the device in (d) allows for at least one of: typing on the touchpad or keyboard of the device, messaging, communicating over a wireless network, using applications on the device, answering phone calls, dialing phone numbers, and other uses of the device that involve the touchpad or keyboard.

10. The method of claim 1, wherein the touchpad or keyboard of the device is directly manipulatable through the opening, and wherein the enclosure is not adapted to enter a sterile field of the operating room.

11. A method comprising:

providing an enclosure having a bag portion and an opening restricting mechanism disposed along a rim of an opening of the bag portion, wherein the bag portion is made of an amount of flexible plastic sheet material, and wherein when the opening of the bag portion is enlarged and a device is placed through the opening and into the bag portion of the enclosure, then a portion of a touchpad or keyboard of the device is exposed to an outer environment through the opening.

12. A method comprising:

providing an enclosure having a bag portion and an opening restricting mechanism disposed along a rim of an opening of the bag portion, wherein the bag portion is made of an amount of flexible plastic sheet material, wherein when the opening of the bag portion is enlarged and a device is placed through the opening and into the bag portion of the enclosure, then a portion of a touchpad or keyboard of the device is exposed to an outer environment through the opening, and wherein the device is taken from the group consisting of: a cellular telephone, a laptop computer, and a tablet computer.

13. The method of claim 11, further comprising:

instructing a user to transport the enclosure containing the device into an operating room.

14. The method of claim 13, further comprising:

instructing the user to use the device in the operating room while the device is disposed in the enclosure such that the portion of the touchpad or keyboard of the device is directly accessible through the opening without contact of any intervening portion of the enclosure, and such that at least part of the touchpad or keyboard of the device is usable by directly contacting the portion of the touchpad or keyboard of the device through the opening without contacting any interior of the enclosure while the device is disposed in the enclosure.

15. A method comprising:

providing an enclosure having a bag portion and an opening restricting mechanism disposed along a rim of an opening of the bag portion, wherein the bag portion is made of an amount of flexible plastic sheet material, wherein when the opening of the bag portion is enlarged and a device is placed through the opening and into the bag portion of the enclosure, then a portion of a touchpad or keyboard of the device is exposed to an outer environment through the opening, and wherein the amount of flexible plastic sheet material is more than eight square inches and is less than forty square inches.

16. The method of claim 11, wherein the flexible plastic sheet material is transparent.

17. The method of claim 11, wherein the flexible plastic sheet material is taken from the group consisting of: a poly vinyl chloride (PVC) material, a polyethylene material, a polypropylene material, a fluorinated hydrocarbon polymer material, a polytetrafluoroethylene (PTFE) material, a silicone rubber material, a nylon material, a flexible silicone composition, a polyamide material, and a polyether block amide material.

18. The method of claim 11, wherein the flexible plastic sheet material comprises an antimicrobial material taken from the group consisting of: an antibacterial material, an antifungal material, and an antiviral material.

19. The method of claim 18, wherein the antimicrobial material protects an operating room from outside biological contaminants and protects an outside of the operating room from biological contaminants within the operating room.

20. The method of claim 18, wherein the antimicrobial material is about 0.0001 percent to about 5 percent by weight of the flexible plastic sheet material.

* * * * *